US011970736B2

(12) United States Patent
Pursiheimo et al.

(10) Patent No.: US 11,970,736 B2
(45) Date of Patent: *Apr. 30, 2024

(54) METHODS FOR ACCURATE PARALLEL DETECTION AND QUANTIFICATION OF NUCLEIC ACIDS

(71) Applicant: Genomill Health Oy, Turku (FI)

(72) Inventors: Juha-Pekka Pursiheimo, Turku (FI); Tatu Hirvonen, Turku (FI); Anttoni Korkiakoski, Turku (FI); Manu Tamminen, Turku (FI)

(73) Assignee: Genomill Health Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 17/899,851

(22) Filed: Aug. 31, 2022

(65) Prior Publication Data

US 2024/0068022 A1    Feb. 29, 2024

(51) Int. Cl.
*C12Q 1/6869* (2018.01)
*C12Q 1/6855* (2018.01)

(52) U.S. Cl.
CPC ......... *C12Q 1/6869* (2013.01); *C12Q 1/6855* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2008/0269068 A1* 10/2008 Church ............... C12Q 1/6874
506/26

FOREIGN PATENT DOCUMENTS

WO        2019038372 A1      2/2019
WO   WO-2019038372 A1 *    2/2019  ........... C12Q 1/6806

OTHER PUBLICATIONS

Deng et al. "DNA-Sequence-Encoded Rolling Circle Amplicon for Single-Cell RNA Imaging" Chem, vol. 4, No. 6, Apr. 12, 2018, ISSN: 2451-9294, DOI: 10.1016/j.chempr.2018.03.003, https://www.sciencedirect.com/science/article/pii/S2451929418302237/pdfft?md5=d7c59008feb30680d87ed3b3436bf590&pid=1-s2.0-S2451929418302237-main.pdf, 14 pages.
European Patent Office, Extended European Search Report, Application No. 23193551.1, mailed Feb. 2, 2024, 6 pages.

* cited by examiner

*Primary Examiner* — Angela M. Bertagna
*Assistant Examiner* — Carolyn L Greene
(74) *Attorney, Agent, or Firm* — Ziegler IP Law Group

(57) ABSTRACT

The present disclosure relates to a next generation DNA sequencing method and use for accurate and massively parallel quantification of one or more nucleic acid targets, for example in large volumes of unpurified sample material. More particularly, the disclosed embodiments is related to a method and a kit comprising probes for detecting and quantifying genetic targets in complex samples. The disclosed embodiments includes two target-specific nucleic acid probes per genetic target, a barcode loop oligo and a bridge oligo or bridge oligo complex.

20 Claims, 7 Drawing Sheets

Specification includes a Sequence Listing.

SEQUENCE LISTING

```
Sequence total quantity: 28
SEQ ID NO: 1            moltype = DNA  length = 31
FEATURE                 Location/Qualifiers
source                  1..31
                        mol_type = other DNA
                        organism = synthetic construct
SEQUENCE: 1
ggggcccgcc gtcgatcgga gccgttagga t                              31

SEQ ID NO: 2            moltype = DNA  length = 31
FEATURE                 Location/Qualifiers
source                  1..31
                        mol_type = other DNA
                        organism = synthetic construct
SEQUENCE: 2
ttaaggtgcc gtcgatcgga gccgacgtac g                              31

SEQ ID NO: 3            moltype = DNA  length = 31
FEATURE                 Location/Qualifiers
source                  1..31
                        mol_type = other DNA
                        organism = synthetic construct
SEQUENCE: 3
ttaaggtgcc gtcgatcgga gccgacgtac g                              31

SEQ ID NO: 4            moltype = DNA  length = 31
FEATURE                 Location/Qualifiers
source                  1..31
                        mol_type = other DNA
                        organism = synthetic construct
SEQUENCE: 4
tataatagag gtcgtgcagt cacgaccsgg t                              31

SEQ ID NO: 5            moltype = DNA  length = 31
FEATURE                 Location/Qualifiers
```

```
source                    1..31
                          mol_type = other DNA
                          organism = synthetic construct
SEQUENCE: 5
accaggtgcc gtcgatcgga gccgacccgg t                                  31

SEQ ID NO: 6              moltype = DNA   length = 31
FEATURE                   Location/Qualifiers
source                    1..31
                          mol_type = other DNA
                          organism = synthetic construct
SEQUENCE: 6
gggccgggag gtcgtgcagt cacgttagga t                                  31

SEQ ID NO: 7              moltype = DNA   length = 31
FEATURE                   Location/Qualifiers
source                    1..31
                          mol_type = other DNA
                          organism = synthetic construct
SEQUENCE: 7
tccaggtgag tcgatccgtc acgtacgtac g                                  31

SEQ ID NO: 8              moltype = DNA   length = 31
FEATURE                   Location/Qualifiers
source                    1..31
                          mol_type = other DNA
                          organism = synthetic construct
SEQUENCE: 8
aaaattttag cgtacgtcgt acgtttagga t                                  31

SEQ ID NO: 9              moltype = DNA   length = 31
FEATURE                   Location/Qualifiers
source                    1..31
                          mol_type = other DNA
                          organism = synthetic construct
SEQUENCE: 9
tataatagag gtcgtgcagt cacgacccgg t                                  31

SEQ ID NO: 10             moltype = DNA   length = 31
FEATURE                   Location/Qualifiers
source                    1..31
                          mol_type = other DNA
                          organism = synthetic construct
SEQUENCE: 10
aggaccttga gtcgatccgc acgtacccgg t                                  31

SEQ ID NO: 11             moltype = DNA   length = 31
FEATURE                   Location/Qualifiers
source                    1..31
                          mol_type = other DNA
                          organism = synthetic construct
SEQUENCE: 11
agcgaccgag gtcgtgcagt cacgacgtac g                                  31

SEQ ID NO: 12             moltype = DNA   length = 31
FEATURE                   Location/Qualifiers
source                    1..31
                          mol_type = other DNA
                          organism = synthetic construct
SEQUENCE: 12
tataatagag gtcgtgcagt cacgacccgg t                                  31

SEQ ID NO: 13             moltype = DNA   length = 31
FEATURE                   Location/Qualifiers
source                    1..31
                          mol_type = other DNA
                          organism = synthetic construct
SEQUENCE: 13
ggaaaaagcc gtcgatcgga gccgttagga t                                  31

SEQ ID NO: 14             moltype = DNA   length = 31
FEATURE                   Location/Qualifiers
source                    1..31
                          mol_type = other DNA
                          organism = synthetic construct
SEQUENCE: 14
atatacagag gtcgtgcagt cacgttagga t                                  31

SEQ ID NO: 15             moltype = DNA   length = 31
```

```
FEATURE                  Location/Qualifiers
source                   1..31
                         mol_type = other DNA
                         organism = synthetic construct
SEQUENCE: 15
gagagccgag gtcgtgcagt cacgacccgg t                              31

SEQ ID NO: 16            moltype = DNA   length = 31
FEATURE                  Location/Qualifiers
source                   1..31
                         mol_type = other DNA
                         organism = synthetic construct
SEQUENCE: 16
cgcacgcgag gtcgtgcagt cacgacgtac g                              31

SEQ ID NO: 17            moltype = DNA   length = 31
FEATURE                  Location/Qualifiers
source                   1..31
                         mol_type = other DNA
                         organism = synthetic construct
SEQUENCE: 17
attacaagcc gtcgatcgga gccgacccgg t                              31

SEQ ID NO: 18            moltype = DNA   length = 31
FEATURE                  Location/Qualifiers
source                   1..31
                         mol_type = other DNA
                         organism = synthetic construct
SEQUENCE: 18
tataatagag gtcgtgcagt cacgacccgg t                              31

SEQ ID NO: 19            moltype = DNA   length = 31
FEATURE                  Location/Qualifiers
source                   1..31
                         mol_type = other DNA
                         organism = synthetic construct
SEQUENCE: 19
gggcaattag cgtacgtcgt acgtacgtac g                              31

SEQ ID NO: 20            moltype = DNA   length = 31
FEATURE                  Location/Qualifiers
source                   1..31
                         mol_type = other DNA
                         organism = synthetic construct
SEQUENCE: 20
tatgcgagcc gtcgatcgga gccgacgtac g                              31

SEQ ID NO: 21            moltype = DNA   length = 31
FEATURE                  Location/Qualifiers
source                   1..31
                         mol_type = other DNA
                         organism = synthetic construct
SEQUENCE: 21
aggaccttga gtcgatccgc acgtacccgg t                              31

SEQ ID NO: 22            moltype = DNA   length = 31
FEATURE                  Location/Qualifiers
source                   1..31
                         mol_type = other DNA
                         organism = synthetic construct
SEQUENCE: 22
attacaagcc gtcgatcgga gccgacccgg t                              31

SEQ ID NO: 23            moltype = DNA   length = 31
FEATURE                  Location/Qualifiers
source                   1..31
                         mol_type = other DNA
                         organism = synthetic construct
SEQUENCE: 23
gaagaattag cgtacgtcgt acgtttagga t                              31

SEQ ID NO: 24            moltype = DNA   length = 31
FEATURE                  Location/Qualifiers
source                   1..31
                         mol_type = other DNA
                         organism = synthetic construct
SEQUENCE: 24
gaagaattag cgtacgtcgt acgtttagga t                              31
```

```
SEQ ID NO: 25          moltype = DNA  length = 31
FEATURE                Location/Qualifiers
source                 1..31
                       mol_type = other DNA
                       organism = synthetic construct
SEQUENCE: 25
gggcaattag cgtacgtcgt acgtacgtac g                                  31

SEQ ID NO: 26          moltype = DNA  length = 31
FEATURE                Location/Qualifiers
source                 1..31
                       mol_type = other DNA
                       organism = synthetic construct
SEQUENCE: 26
gagcacttag cgtacgtcgt acgtacccgg t                                  31

SEQ ID NO: 27          moltype = DNA  length = 31
FEATURE                Location/Qualifiers
source                 1..31
                       mol_type = other DNA
                       organism = synthetic construct
SEQUENCE: 27
aaagggcga gtcgatccgc acgtttagga t                                   31

SEQ ID NO: 28          moltype = DNA  length = 31
FEATURE                Location/Qualifiers
source                 1..31
                       mol_type = other DNA
                       organism = synthetic construct
SEQUENCE: 28
agcgcgcgcc gtcgatcgga gccgttagga t                                  31
```

METHODS FOR ACCURATE PARALLEL DETECTION AND QUANTIFICATION OF NUCLEIC ACIDS

INCORPORATION BY REFERENCE

The sequence listing in XML format is incorporated herein by reference in its entirety.
   a. Name of File: Genomill005 ST26 SequenceListing to be filed
   b. Date of Creation: 5 Aug. 2022
   c. Size of File: 25,000 Bytes

TECHNICAL FIELD

The present invention disclosure relates to improved next generation DNA sequencing methods for accurate and massively parallel quantification of one or more nucleic acid targets. More particularly, the disclosure is related to methods and kits comprising probes for detecting and quantifying genetic targets in complex DNA pools primarily used for genetic target and variant detection. The invention uses one or more target-specific nucleic acid probes per genetic target, a barcode loop oligo and one or more bridge oligos.

BACKGROUND

With the advancement in the technology to study genetic variation, detection of the same in plants and animals is not cumbersome. However, detecting and accurately quantifying genetic variations such as mutations, in particular in samples having weak signals is currently still cumbersome, laborious and expensive, despite decreased sequencing costs. Various problems can be expressed more accurately such as specificity in order to detect genetic signals against a consensus background, sensitivity in order to detect weak genetic signals, accuracy for accurate quantification of the detected signals, throughput number of targeted genetic targets per assay, cost per assay, scaling to determine the assay cost scale when assaying multiple samples in parallel and turn-over to determine how long is the time from sampling to the results.

Currently, the typical quantification methods for liquid biopsies and conceptually similar assays (such as antibiotic resistance gene detection) include quantitative PCR (qPCR), array qPCR, digital PCR, Multiplex Ligation-dependent Probe Amplification (MLPA) or quantification from next-generation DNA sequencing data. While the quantification methods are robust and well-established methods, each of the method is associated with specific problems discussed in closer detail below:

Quantitative PCR: Quantitative PCR (qPCR), is a technique which includes the amplification of a targeted DNA molecule during the PCR, i.e. in real-time. Real-time PCR can be used quantitatively (quantitative real-time PCR), and semi-quantitatively, i.e. above/below a certain amount of DNA molecules (semi quantitative real-time PCR). Quantitative PCR (qPCR) is a gold standard of genetic target quantification. Currently, the laboratory cost of a qPCR reaction is approximately $2. However, counting in the considerable hands-on time (labour cost) for setting up the reaction, the need for standard curves, along with replicates for each quantified target, the real cost is in fact much higher. The amount of hands-on time scales steeply with an increasing number of samples since a separate quantification experiment is required for each genetic target.

Array PCR: PCR Arrays are the most reliable tools for analyzing the expression of a relevant pathway- or disease-focused panel of genes. Each 96-well plate, 384-well plate, or 100-well disc PCR Array includes SYBR Green-optimized primer assays for a thoroughly researched panel of focused panel of genes. A newer iteration of the qPCR technology is array qPCR which miniaturizes the individual qPCR reactions. Array PCR brings down the cost of an individual qPCR reaction and improves the scalability of the method to multiple targets and samples. However, the method is currently limited to profiling 384 targets from 12 samples (or conversely 12 targets from 384 samples) at a cost of thousands of dollars per chip plus a large capital cost of the read-out infrastructure. Profiling thousands of samples using the aforementioned setup, therefore, remains prohibitively expensive.

Digital PCR: Digital polymerase chain reaction (digital PCR, DigitalPCR, dPCR, or dePCR) is a method to provide absolute quantification of targets through droplet-microfluidics and fluorescent detection. The methodology is relatively cost-effective (one target per sample costs around $3), but the hands-on time for preparing, setting-up and running individual experiments for each target in each sample scales poorly to thousands of samples.

Multiplex Ligation-dependent Probe Amplification (MLPA) provides an approach to simplify the detection of multiple genetic targets in individual samples. However, MLPA provides only relative quantification of targets, and requires a separate detection experiment for each sample. More recently, a variant of MLPA introduces concepts from DNA barcoding. The concept permits a better quantitative resolution and sample multiplexing than the traditional MLPA workflow.

Next generation sequencing-based approaches: Next-generation sequencing (NGS), also known as high-throughput sequencing that makes sequence-based gene expression analysis a "digital" alternative to analog techniques. Target counting from next-generation DNA sequencing data is becoming increasingly attractive as the cost of DNA sequencing keeps decreasing, and is currently used for instance in noninvasive prenatal testing. However, the current approach suffers from high sequencing library preparation costs and sequencing efforts that is wasted on sequencing non-relevant genetic targets. For instance, in cancer-related liquid biopsies, non-targeted approaches result in wastage of sequencing effort on oncologically non-relevant loci. In fetal diagnostics, non-targeted sampling of loci considerably limits the statistical options for interpreting the data. Guardant Health Inc provides more targeted sequencing approach, where an array of RNA capture probes enriches targets for next-generation DNA sequencing.

Akhras et al. (2007) PLoS ONE 2(2): e223 disclose a multiplex pathogen detection assay involving barcoded target-specific probes, target circularization and sequencing. Use of a bridging oligonucleotide to ligate the target-specific probes is also disclosed.

WO2018109206 describes methods for the detection of analytes in a sample using padlock probes and rolling circle amplification. The use of a bridging oligo is not described.

WO2019038372 describes a next-generation sequencing approach wherein target sequences of interest are selectively amplified by in vitro transcription from ligation complexes containing a promoter for T7 polymerase, followed by cDNA synthesis and sequencing. While this method allows accurate and parallel detection and quantification of many target sequences in a sample, more complex, large volume, dilute and/or impure samples remain challenging.

Therefore, in light of the foregoing discussion, there exists a need to overcome the aforementioned drawbacks such as, but not limited to, specificity, sensitivity, accuracy, throughput, cost, scaling and turn-over through an accurate and massively parallel quantification of nucleic acid targets.

SUMMARY OF THE INVENTION

The present invention provides a method for using next-generation sequencing for highly sensitive, scalable and accurate target quantification from large volume samples (up to tens of milliliters) and/or dilute and/or non-purified sample material. An RNA amplification step such as described in WO2019038372 is avoided, rendering the method more simple. Furthermore, the method of the present invention includes the use of a separate barcode loop oligonucleotide for sample identification. The use of a barcode loop oligonucleotide permits simultaneous target querying and sample indexing, permitting an efficient sample pooling and consequently more cost-efficient and flexible quantification assay and provides an alternative way to introduce unique molecular identifier (UMI) sequences. The resulting protocol omits the requirement for separate sample indexing, therefore permitting shorter read lengths and providing benefits to both short read and nanopore sequencing applications.

In a first main aspect, the invention relates to a method for the high-throughput detection of one or more target nucleotide sequence in a plurality of samples, the method comprising the steps of:

(i) providing for each target nucleotide sequence in each of the samples: a first probe, a second probe, a barcode loop oligo and a bridge oligo or a plurality of bridge oligonucleotides capable of annealing to the barcode loop oligo to form a bridge oligo complex,
wherein the first probe comprises a first bridge oligo-specific sequence at the 5' end of the first probe and a first target specific portion at the 3' end of the first probe;
wherein the second probe comprises a second target specific portion at the 5' end of the second probe and a second bridge oligo-specific sequence at the 3' end of the second probe;
wherein the barcode loop oligo comprises, starting from the 5' end of the molecule, a third bridge oligo-specific sequence, a barcoded loop sequence and a fourth bridge oligo-specific sequence,
wherein the bridge oligo or plurality of bridge oligonucleotides contains sequences complementary to the first bridge oligo-specific sequence and the second bridge oligo-specific sequence in the first probe and the second probe, respectively, and sequences complementary to the third bridge oligo-specific sequence and the fourth bridge oligo-specific sequence in the barcode loop oligo;
and wherein, optionally, at least one of: the first probe, the second probe, the barcode loop oligo, the bridge oligo or an oligonucleotide of the plurality of bridge oligonucleotides comprises a recognition sequence for an endonuclease;

(ii) contacting, for each of the one or more target nucleotide sequence, the first probe and the second probe with, preferably for each of the samples in a separate tube, the barcode loop oligo and the bridge oligo or plurality of bridge oligonucleotides, and allow self-annealing into ligation complexes;

(iii) contacting nucleic acids present in each of the samples to be tested for the target nucleotide sequences with the ligation complexes;

(iv) allowing the first target specific portion and the second target specific portion of the respective first probe and the second probe to hybridize to essentially adjacent sections on the target sequence, thereby forming hybridization complexes;

(v) optionally pooling the hybridization complexes from the plurality of samples;

(vi) ligating the probes in the hybridization complexes to provide ligated ligation complexes;

(vii) amplifying nucleic acids from the one or more ligated ligation complexes using rolling circle amplification with a strand-displacing polymerase thereby obtaining single-stranded concatemeric sequences;

(viii) optionally, provided a recognition sequence as specified in step (i) is present, performing a step to obtain nucleic acid fragments by:
   (a) cleaving the single-stranded concatemeric sequences obtained in step (vii), or
   (b) subjecting the single-stranded concatemeric sequences obtained in step (vii) to annealing with a specific oligonucleotide containing a recognition sequence for an endonuclease wherein the oligonucleotide anneals with the recognition sequence specified in step (i) such that a recognition site for the endonuclease is obtained and cleaving the annealed complexes with said endonuclease;

(ix) subjecting the concatemeric sequence obtained in step (vii) or the nucleic acid fragments obtained in step (viii) to high-throughput sequencing technology to determine the barcode sequence(s); and (x) identifying the presence and/or number of the target nucleotide sequence in the plurality of samples by determination of at least part of the first target specific portion and/or the second target specific portion, and/or at least part of the barcode sequence corresponding to the barcode in the barcode loop oligo, wherein steps (v) and (vi) may be performed in any order.

DETAILED DESCRIPTION OF THE INVENTION

Definitions

Figure 1:
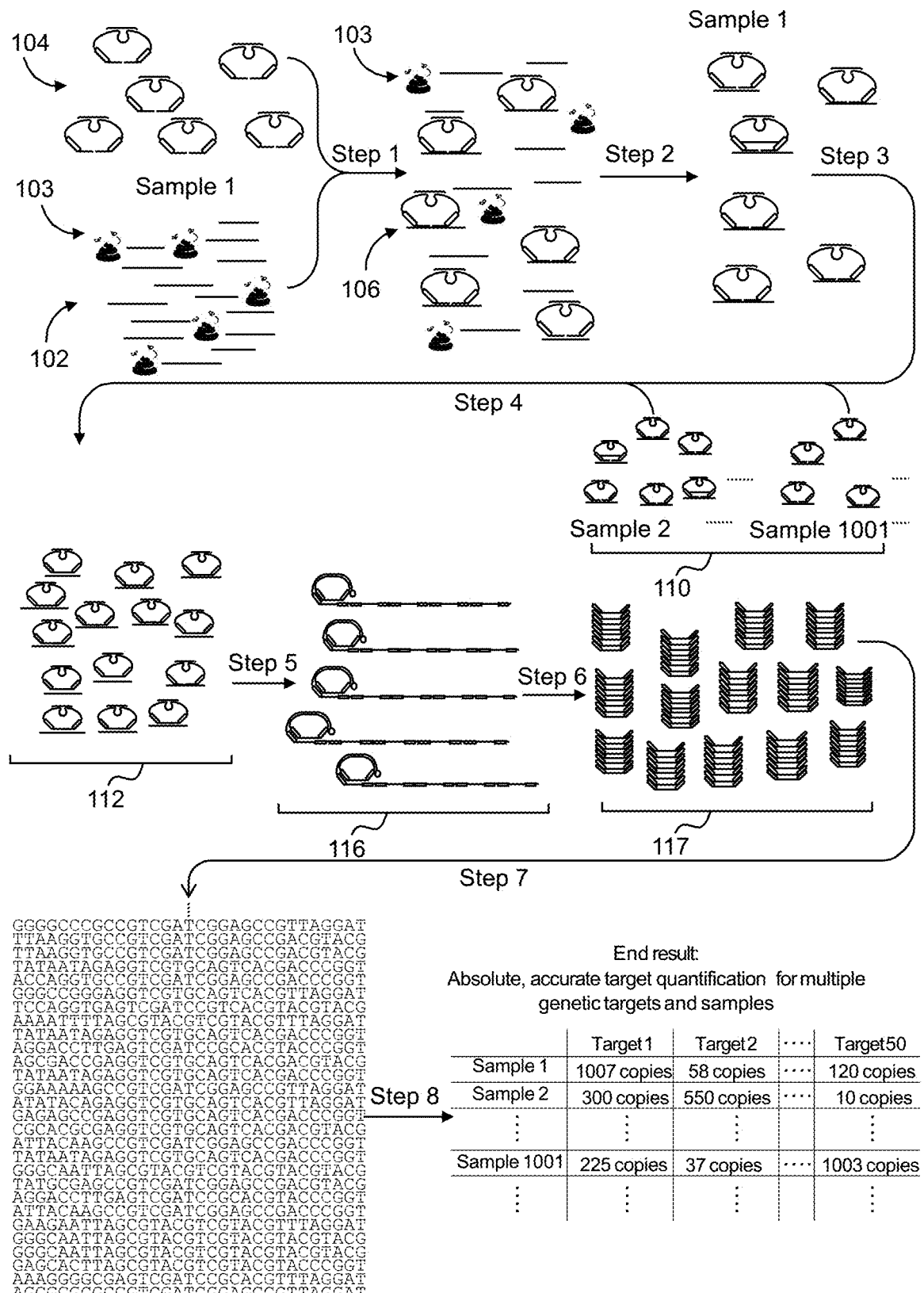
FIG. 1 illustrates a flow diagram of the Multiplexed Ligation Assay (MLA) according to an embodiment of the invention including SEQ ID Numbers 1, 2, 3, 4, 5, 6, 7, 8, 9, 10, 11, 12, 13, 14, 15, 16, 17, 18, 19, 20, 21, 22, 23, 24, 25, 26, 27 and 28.

Target Nucleotide Sequence: The term target nucleotide sequence may be any nucleotide sequence of interest of which its detection is required. It will be understood that the term given refers to a sequence of contiguous nucleotides as well as to nucleic acid molecules with the complementary sequence. The target sequence in some embodiments is a nucleotide sequence that represents or is associated with a polymorphism.

Polymorphism: The term polymorphism refers to an occurrence of two or more genetically determined alternative sequences or alleles in a population. A polymorphic marker or site is the locus at which sequence divergence occurs. A polymorphic locus may be as small as one base pair. Samples: The term samples is used herein for two or more samples which contain two or more target sequences. Samples as provided in a method according to the invention may have been prepared in order to extract at least the target nucleic acids and make those accessible to the probes as used in the invention. In particular, in some embodiments, the samples each comprise at least two different target sequences, preferably at least 100, more preferably at least 250, more preferably at least 500, most preferably at least 2000, or more. The term samples may refer to but is not limited to two or more samples obtained from a human/animal body, including urine, biopsies, saliva and other secretions, exhaled moisture extracts, tissue, blood plasma (liquid biopsies), or two or more samples obtained from the environment, including water, wastewater, soil, plants, or two or more samples containing viruses or bacteria or the like. In one embodiment, the plurality of samples includes a blood sample, a saliva sample, a urine sample or a feces sample, a sample of another body fluid or an extract from body material, for example hair or skin flakes. Probe: The term probe is a fragment of DNA or RNA of variable length (usually 50-1000 bases long, preferably 50-200 bases long) which can be used in DNA or RNA samples to detect the presence of nucleotide sequences (the DNA or RNA target) that are complementary to the sequence in the probe. The sections of the oligonucleotide probes that are complementary to the target sequence are designed such that for each target sequence in a sample, a pair of a first and second probe is provided, whereby the probes each contain a section at their extreme end that is complementary to a part of the target sequence. Furthermore, the present disclosure describes a bridge oligo or bridge oligo complex that is used for joining the first probe and the second probe. Moreover, the present disclosure describes a barcode loop oligo that comprises a loop section flanked by two sections that can hybridize with the one or more bridge oligo. The loop section does not hybridize with the one or more bridge oligo and comprises a barcode.

Universal: The term universal when used to describe an amplification procedure refers to a sequence that enables the use of a single primer or set of primers for a plurality of amplification reactions. The use of such primers greatly simplifies multiplexing in that only two primers are needed to amplify a plurality of selected nucleic acid sequences. The term universal when used to describe a priming site is a site to which a universal primer will hybridize. It should also be noted that "sets" of universal priming sequences/primers may be used.

Hybridization: The term hybridization (or hybridisation) describes the process of DNA or RNA molecules annealing to complementary DNA or RNA. DNA or RNA replication and transcription of DNA into RNA both rely on nucleotide hybridization.

Ligation: The term ligation is the joining of two nucleic acid fragments through the action of an enzyme. DNA ligases are enzymes capable of catalyzing the formation of a phosphodiester bond between (the ends of) two polynucleotide strands bound at adjacent sites on a complementary strand. In one embodiment, ligation can also be performed chemically, in particular if both adjacent ends of the polynucleotides are modified to allow chemical ligation.

Amplification: The term amplification as used herein denotes the use of a DNA polymerase to increase the concentration of a particular nucleotide sequence within a mixture of nucleotide sequences. "PCR" or "Polymerase Chain Reaction" is a rapid procedure for in vitro enzymatic amplification of a specific DNA/RNA segment. The DNA/RNA to be amplified may be denatured by heating the sample. The term primer is a strand of RNA or DNA (generally about 18-22 bases) that serves as a starting point for DNA synthesis. It is required for DNA replication because the enzymes that catalyze this process, DNA polymerases, can only add new nucleotides to an existing strand of DNA.

Polymerase: A polymerase is an enzyme that synthesizes long chains or polymers of nucleic acids. DNA polymerase and RNA polymerase are used to assemble DNA and RNA molecules, respectively, by copying a DNA or RNA template strand using base-pairing interactions.

High throughput: The term high throughput denotes the ability to simultaneously process and screen a large number of DNA samples; as well as to simultaneously screen large numbers of different genetic loci within a single DNA sample. High-throughput sequencing or screening, often abbreviated as HTS is a method for scientific experimentation especially relevant to effectively screen large amounts of samples simultaneously.

Endonuclease: An endonuclease is an enzyme that cleaves or nicks DNA double or single strand at a random or specified location.

Barcode: Probes and oligos used in the present invention may comprise one or more barcodes consisting of nucleotide sequences. Barcode sequences may comprise target nucleotide sequence identifier sequences, sample identifier sequences and/or molecular barcodes (also termed Unique Molecular Identifiers) for target enumeration. Barcode sequences may comprise random sequences.

As described above, the disclosure relates to a method for the high-throughput detection of target nucleotide sequence detection in a very large number of samples by leveraging ligation-dependent assays. The disclosure provides a method for determining the sequences of genetic targets in complex nucleic acid pools using techniques permitted by next generation sequencing. The disclosure also provides a method to profile multiple genetic targets in a number of samples, preferably a very large number of samples, by leveraging ligation-dependent assays. The disclosure provides a method for the multiplex ligation-dependent probe amplification enabling querying different target nucleic acids in a plurality of samples. The methods of the present invention allow the sequencing of the one or more target nucleotide sequence in a plurality of samples providing a plurality of different probe sets for different target nucleic acids. Unique sequence identifiers are used for the identification of the genetic targets and absolute quantification of individual samples from the sample pool when processing the sequencing data.

In a first main aspect, the invention relates to a method for the high-throughput detection of one or more target nucleotide sequence in a plurality of samples, the method comprising the steps of:
(i) providing for each target nucleotide sequence in each of the samples: a first probe, a second probe, a barcode loop oligo and a bridge oligo or a plurality of bridge oligonucleotides capable of annealing to the barcode loop oligo to form a bridge oligo complex,
wherein the first probe comprises a first bridge oligo-specific sequence at the 5' end of the first probe and a first target specific portion at the 3' end of the first probe;
wherein the second probe comprises a second target specific portion at the 5' end of the second probe and a second bridge oligo-specific sequence at the 3' end of the second probe;
wherein the barcode loop oligo comprises, starting from the 5' end of the molecule, a third bridge oligo-specific sequence, a barcoded loop sequence and a fourth bridge oligo-specific sequence,
wherein the bridge oligo or plurality of bridge oligonucleotides contains sequences complementary to the first bridge oligo-specific sequence and the second bridge oligo-specific sequence in the first probe and the second probe, respectively, and sequences complementary to the third bridge oligo-specific sequence and the fourth bridge oligo-specific sequence in the barcode loop oligo;
and wherein, optionally, at least one of: the first probe, the second probe, the barcode loop oligo, the bridge oligo or an oligonucleotide of the plurality of bridge oligonucleotides comprises a recognition sequence for an endonuclease;
(ii) contacting, for each of the one or more target nucleotide sequence, the first probe and the second probe with, preferably for each of the samples in a separate tube, the barcode loop oligo and the bridge oligo or plurality of bridge oligonucleotides, and allow self-annealing into ligation complexes;
(iii) contacting nucleic acids present in each of the samples to be tested for the target nucleotide sequences with the ligation complexes;
(iv) allowing the first target specific portion and the second target specific portion of the respective first probe and the second probe to hybridize to essentially adjacent sections on the target sequence, thereby forming hybridization complexes (or optionally a hybridization complex);
(v) optionally pooling the hybridization complexes from the plurality of samples;
zo (vi) ligating the probes in the hybridization complexes to provide ligated ligation complexes;
(vii) amplifying nucleic acids from the one or more ligated ligation complexes using rolling circle amplification with a strand-displacing polymerase thereby obtaining single-stranded concatemeric sequences;
(viii) optionally, provided a recognition sequence as specified in step (i) is present, performing a step to obtain nucleic acid fragments by:
(a) cleaving the single-stranded concatemeric sequences obtained in step (vii), or
(b) subjecting the single-stranded concatemeric sequences obtained in step (vii) to annealing with a specific oligonucleotide containing a recognition sequence for an endonuclease wherein the oligonucleotide anneals with the recognition sequence specified in step (i) such that a recognition site for the endonuclease is obtained and cleaving the annealed complexes with said endonuclease;
(ix) subjecting the concatemeric sequence obtained in step (vii) or the nucleic acid fragments obtained in step (viii) to high-throughput sequencing technology to determine the barcode sequence(s); and
(x) identifying the presence and/or number of the target nucleotide sequence in the plurality of samples by determination of at least part of the first target specific portion and/or the second target specific portion, and/or at least part of the barcode sequence corresponding to the barcode in the barcode loop oligo,
wherein steps (v) and (vi) may be performed in any order.

FIG. 1 provides a non-limiting illustration of an embodiment of the method of the invention.

The methods of the present invention utilize four or more nucleic acid molecules, out of which two target-specific nucleic acid probes (first probe and second probe) are specific for a genetic target and two or more other nucleic acid probes typically are universal (bridge oligo or bridge oligo complex and barcode loop oligo). The first probe, second probe and barcode loop oligo hybridize to the one or more bridge probe forming a ligation complex. The ligation complexes (containing one or more barcode sequences) having target identification sites on the sample DNA or RNA are allowed to hybridize against complementary target sequences of the query sample. After hybridization, the first and second probe are ligated chemically or enzymatically by a DNA ligase to form ligated ligation complex. In the present invention, a plurality of such ligated ligation complexes will form during the sample analysis in the plurality of samples to be analyzed.

A "plurality of samples" may refer to, but is not limited to, two or more samples obtained from the human or animal body, including biopsies, saliva and other secretions, exhaled moisture extracts, tissue, blood plasma (liquid biopsies), two or more samples obtained from environment, including water, wastewater, soil, plants, or two or more samples containing viruses or bacteria or the like. In one embodiment, the sample is used without any prior purification or concentration of nucleic acid. In another embodiment, the sample may be pre-treated, for instance lysing cells to expose nucleic acid.

The target sequence may include any nucleotide sequence of interest against which the detection is required. The target nucleotide sequence of the disclosure may be obtained from, but not limited to, a fraction of DNA in the patient's blood or a fraction of DNA in maternal blood. A fraction of the DNA in the patient's blood may for example be obtained from apoptotic/necrotic cancer cells or a fraction of DNA in maternal blood from fetal and/or maternal origin. Further, the results of the analysis are used to, for instance, assess the risk of an individual to a given type of cancer, to determine the efficacy of a given treatment against a given cancer, the development of a drug-resistance-related mutations in a tumor, or the risk of a fetus carrying genetic disorders such as common trisomies Down, Patau and Edwards syndromes. In certain embodiments, the method comprises providing, for each target nucleotide sequence, a plurality of different probe sets.

As used herein, the term probe sets includes a first probe, a second probe, barcode loop oligo and one or more bridge oligo.

In certain embodiments, the first probe includes, starting from the 5' end of the molecule, optionally a 5' phosphate, a first bridge oligo-specific sequence, optionally a first universal sequence, optionally a first sequence barcode, and a first target specific portion at its 3' end.

In certain embodiments, the second probe includes, starting from 5' end of the molecule, optionally a 5' phosphate, a second target specific portion, optionally a second sequence barcode, optionally a second universal sequence, and a second bridge oligo-specific sequence at its 3' end.

The bridge oligo or plurality of bridge oligos contains sequences complementary to the first and second bridge oligo-specific sequences in the first and second probe, respectively, optionally a universal sequence and sequences complementary to the third bridge oligo-specific sequence and the fourth bridge oligo-specific sequence in the barcode loop oligo.

The barcode loop oligo comprises starting from the 5' end of the molecule, a third bridge oligo-specific sequence, a barcoded loop sequence and a fourth bridge oligo-specific sequence. The barcode may be used to enable to uniquely define the complex within all ligation complexes in all samples tested. The barcode loop oligo may have any suitable length and may, for example, be between 30 and 100 bp in length, such as between 40 and 60 bp in length.

Optionally, at least one of: the first probe, the second probe, the barcode loop oligo or the one or more bridge oligo comprises a recognition sequence for an endonuclease. An endonuclease recognition sequence enables the cleavage of the concatemeric sequence. In one embodiment, the recognition sequence is a recognition sequence for a restriction endonuclease such as EcoRI. In another embodiment, the recognition sequence is a recognition sequence for a homing endonuclease such as I-CeuI. In another embodiment the recognition sequence is a recognition sequence for a guided DNAaseI or CRISPR-Cas-like cleavage system. In another embodiment, the recognition sequence is a recognition sequence for a nicking endonuclease.

In one embodiment, the barcode loop oligo contains one or more recognition sequences for an endonuclease, such as a nicking endonuclease. In a further embodiment, said barcode loop oligo contains two recognition sequences that are capable of annealing to each other such that a double-stranded endonuclease recognition site is obtained. In a further embodiment hereof, the method does not comprise step (viii) as specified above, but (instead) comprises, between steps (vii) and (ix), a step of allowing two recognition sequences in the barcode loop oligo to anneal and cleaving the resulting double-stranded endonuclease recognition site with an endonuclease, such as a nicking endonuclease, having specificity for said recognition site.

Optionally, at least one of: the first probe, the second probe, the barcode loop oligo or the one or more bridge oligo comprises a first capture moiety. A first capture moiety, when used herein, refers to a moiety, such as a chemical group, which allows the probe, ligation complex or hybridization complex to be captured by, i.e. bound to, a second capture moiety which is linked to a solid support. Any suitable capture moiety known in the art may be used for this purpose. A well-known suitable example is the capture of biotinylated molecules using streptavidin-coated magnetic beads. Thus, in one embodiment, the first capture moiety is a biotin moiety, which can interact with a streptavidin or avidin moiety (the second capture moiety) linked to a solid support, such as a magnetic bead. Other options include biotin derivatives such as dual-biotin, desthiobiotin or photocleavable biotin which can be used for conjugation with streptavidin/avidin. Further options include the use of thiol and acrydite groups for acrydite/acrylamide conjugation, alkyne and azide groups for click chemistry and digoxigenin for anti-digoxigenin antibody conjugation. The conjugation partners can be provided on any solid surfaces such as beads (magnetic or otherwise) or solid supports. Accordingly, in one embodiment of the method of the invention, at least one of: the first probe, the second probe, the barcode loop oligo or the one or more bridge oligo comprises a first capture moiety, and between steps (iv) and (v) an intermediate step (iv)(a) is performed which comprises bringing the hybridization complex(es) in contact with a solid support comprising a second capture moiety, allowing the first capture moiety and the second capture moiety to interact such that the hybridization complexes become linked to the solid support and separating the solid-support-linked hybridization complexes from components of the samples that are not linked to the solid-support.

Figure 3:
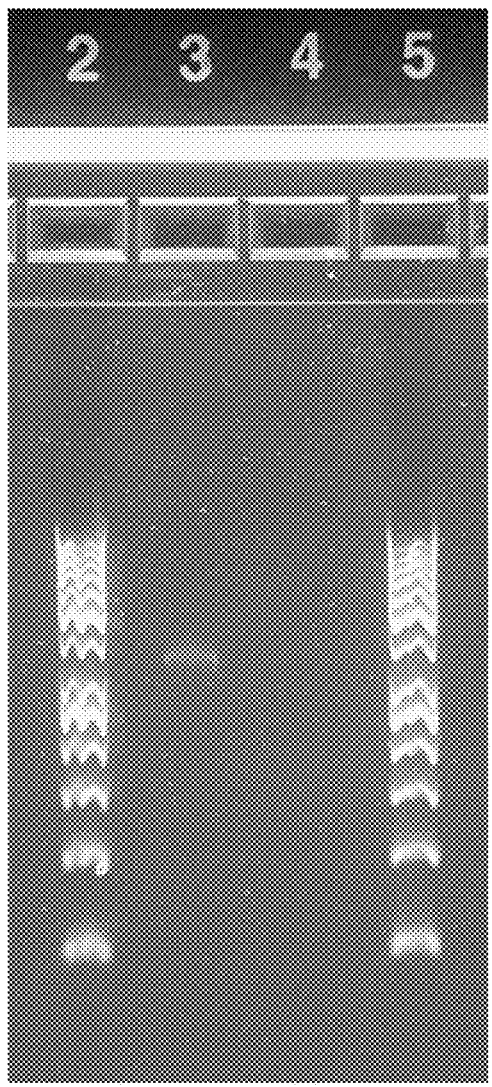
FIG. 3 illustrates the RCA products from the workflow before (lane 2) and after (lane 1) digestion by a restriction endonuclease.

The first target specific portion, the second target specific portion, the first bridge oligo-specific sequences, the second bridge oligo-specific sequences, the third bridge oligo-specific sequences and/or the fourth bridge oligo-specific sequences, optionally contain independently from one another at least one chemically modified nucleotide to increase probe binding. The chemical modifications that increase probe binding include, but are not limited to, ribonucleic acids, peptide nucleic acids, and locked nucleic acids (e.g. as illustrated in FIG. 3 of WO2019038372, incorporated herein by reference). In one embodiment, the bridging portion of the first probe, the second probe, the barcode loop oligo or all three of these, comprise(s) chemically modified bases to permit improved binding to the one or more bridge oligo. In another embodiment, the first target specific portion, the second target specific portion, the first bridge oligo-specific sequences, the second bridge oligo-specific sequences, the third bridge oligo-specific sequences and/or the fourth bridge oligo-specific sequences contain independently from one another, one or more chemically modified nucleotides. In certain embodiments, chemical modifications permit chemical ligation of adjacent probes.

In some embodiments, the aforementioned probes bind to completely adjacent genetic loci, i.e. adjacent sections of the target nucleotide sequence, or up to 500 base pairs apart, for example up to 200 base pairs apart, such as up to 50 base pairs apart, up to 40 base pairs apart, up to 30 base pairs apart, up to 20 base pairs apart up to 10 base pairs apart or up to 5 base pairs apart.

In some embodiments, the first probe, the second probe, the barcode loop oligo or the one or more bridge oligo may include adapter sequences for a DNA sequencing platform such as (but not limited to) Illumina. These adapter sequences permit the resulting sequencing libraries to bind to the detection parts of the sequencing devices such as Illumina flow cells.

Furthermore, in some embodiments, the bridge oligo or an oligonucleotide of the plurality of bridge oligonucleotide comprises:
 (i) one to five 3' protruding bases (i.e. additional bases which do not form double helix with the second probe), and/or
 (ii) 3' phosphate, and/or
 (iii) one or more phosphorothioate modifications within three positions from the 3' end.

Before contacting the probes with the sample comprising the target sequences, the first probe, the second probe and the barcode loop oligo are brought in contact with the bridge oligo (or plurality of oligonucleotides capable of forming a bridge oligo complex), preferably for each of the samples in a separate tube, and annealing into ligation complexes is allowed (step (ii)). The bridge oligo and the barcode loop may be pre-annealed before annealing with the first and second probes or all annealing steps may be done at once. In an embodiment wherein the bridge is not one oligo, but a plurality of oligonucleotides, such as two oligonucleotides, capable of annealing to the barcode loop oligo to form a bridge oligo complex (illustrated herein in 2B), the plurality of oligonucleotides may be pre-annealed with the barcode loop oligo before annealing with the first and second probes or all annealing steps may be done at once or the barcode loop oligo can be annealed to the pre-annealed probe complex during target capture.

Preferably each ligation complex is unique for the combination of the first target specific sequence, the second target specific sequence and one or more barcode sequences. This enables enumeration of the target sequences after amplification and analysis of the results.

Thereafter, one or more target nucleotide sequences in the plurality of samples is brought into contact with the plurality of ligation complexes (step (iii)). The first target specific portion and the second target specific portion of the respective first probe and the second probe hybridize to adjacent sections on the target sequence, thereby forming a hybridization complex (step (iv)). As mentioned above, the essentially adjacent sections on the target sequence may be immediately adjacent or there may be a gap of up to 500 base pairs apart.

In some embodiments, the sample has a volume of more than 100 microliters, e.g. more than 1 ml. In a further embodiment, the sample has a nucleic acid concentration below 5 pmol, such as below 1 pmol, for example below 200 fmol. In one embodiment, the plurality of samples includes one or more blood samples, one or more saliva samples, one or more urine samples or one or more feces samples.

Subsequently, in some embodiments, if at least one of: the first probe, the second probe, the barcode loop oligo or the one or more bridge oligo comprises a first capture moiety, the hybridization complex(es) are brought in contact with a solid support comprising a second capture moiety and the first capture moiety and the second capture moiety are allowed to interact such that the hybridization complex(es) become linked to the solid support (optional step (iv)(a)). Thereafter, the solid-support-linked hybridization complexes are separated from components of the samples that are not linked to the solid-support. If the solid supports are magnetic beads, the beads may be immobilized using a magnet and the remaining liquid sample may be removed. Optionally, a wash step is performed before proceeding.

Step (iv)(a) results in a purification and enrichment for nucleic acid, allowing improved results in particular for highly impure samples. In one embodiment, the method of the invention does not comprise a step of enriching for nucleic acids prior to step (iv)(a). Thus, in one embodiment, the method does not contain prior to step (vi) a step wherein nucleic acids in the original sample are concentrated more than 2-fold, more than 10-fold, or more than 100-fold. In another embodiment, the method of the invention does not include a purification step subsequent to the ligation in step (vi).

Subsequently, ligation of the probes in the formed hybridized complexes is carried out either enzymatically or chemically to provide ligated ligation complexes (step (vi)). Optionally as a part of step (vi), a gap between the first probe and the second probe, between the first probe and the barcode loop oligo and/or between the second probe and the barcode loop oligo, if present, may be filled by introducing a polymerase and one or more nucleotides. The polymerase adds nucleotides (a) complimentary to the bridge oligo sequence(s) and thereby fills in the gaps between the first probe, the second probe and the barcode loop oligo resulting in ligated the probes and inclusion of the barcode loop oligo into the bridge complementary strand. The bridge oligo or bridge oligo complex is extended from the 5' site or the 3' site complimentary to the ligated probes such that the target sequence identifier sequence present in the first probe or second probe is integrated into the bridge oligo or bridge oligo complex. Preferably, a polymerase is used that does not break up double stranded DNA, such as for instance a Taq polymerase, in order not to interfere with the ligation of the first to the second probe when both are annealed to the target sequence. In one embodiment, the bridge oligo, or one or more oligonucleotides of the plurality of bridge oligonucleotides, comprises, in a region not complementary to the first probe, the second probe or the barcode loop oligo, a plurality of universal base analogues to permit the incorporation of random sequences suitable for use as molecular barcode for target enumeration. In such an embodiment, as part of step (vi), a gap filling step is performed using polymerase and nucleotides in order to generate such random sequences. In embodiment, plurality of universal base analogues is a plurality of 5-nitroindoles.

The ligated ligation complexes are then optionally pooled from one or more target samples (step (vi)). Steps (v) and (vi) may be performed in the specified order or alternatively in reverse order.

Next, nucleic acids are amplified from the one or more ligated ligation complexes, thereby obtaining single-stranded concatemeric sequences (step (vii)). Amplification is performed using rolling circle amplification with a strand-displacing polymerase, such as phi29 polymerase (UniProtKB-P03680; DPOL_BPPH2) or a Bst polymerase (P52026; DPO1_GEOSE).

In one embodiment, subsequent to step (vi), but prior to step (vii), a step (a) and a step (b) are performed, wherein step (a) comprises allowing the ligated ligation complexes to dissociate from the target nucleotide sequence and step (b) comprises adding a target-specific probe comprising a sequence corresponding to the target nucleotide sequence, wherein said target-specific probe is capable of annealing with the ligated ligation complexes, and allowing the target-specific probe to anneal to the ligated ligation complexes thereby forming amplification templates. In such an embodiment, said amplification templates are amplified by rolling circle amplification with a strand-displacing polymerase in step (vii).

Optionally, provided a recognition sequence as specified in step (i) is present, a step (viii) is performed to obtain nucleic acid fragments by:
  (a) cleaving the single-stranded concatemeric sequences obtained in step (vii), or
  (b) subjecting the single-stranded concatemeric sequences obtained in step (vii) to annealing with a specific oligonucleotide containing a recognition sequence for an endonuclease wherein the oligonucleotide anneals with the recognition sequence specified in step (i) such that a recognition site for the endonuclease is obtained and cleaving the annealed complexes with said endonuclease.

Subsequently, in step (ix), the concatemeric sequences obtained in step (vii) or, if step (viii) was performed, the nucleic acid fragments obtained in step (viii), are subjected to high-throughput sequencing technology to determine the barcode sequence(s).

Optionally, after amplification, the solid supports, if present, are removed and the supernatant is used for subsequent processing. For example, if the solid supports are magnetic particles, these may be removed using a magnet. In some other embodiments of the method of the invention, the interaction between the first capture moiety and the second capture moiety is disrupted immediately after step (v), after step (vi) or after step (vii). For example, if the first capture moiety is biotin and the second capture moiety is streptavidin, the interaction can be disrupted by adding excess soluble biotin. If the streptavidin is bound to magnetic particles, it can subsequently be removed using a magnet.

Furthermore, optionally, a PCR amplification is performed immediately prior to step (ix) using primers which bind to universal parts of the first and second probes, wherein said primers optionally include adapter sequences for the subsequent sequencing in step (ix).

In another embodiment, the sequencing in step (ix) is performed using nanopore sequencing, wherein optionally the concatemeric sequence obtained in step (vii) is fragmented using transposition complexes. Suitable techniques for nanopore sequencing have been reviewed in Wang et al. (2021 Nat Biotechnol 39(11):1348.

The identification of the presence and/or number of the target nucleotide sequence in the plurality of samples may be performed by determination of at least part of the first and/or second target specific portion, and/or at least part of a barcode by high-throughput sequencing technology (steps (ix) and (x)), for example using a next-generation sequencing platform including without limiting, Illumina iSeq, MiSeq, HiSeq, NextSeq or NovaSeq. Preferably, the genetic target enumeration is permitted by counting the number of molecular barcodes per target and per sample. The samples are separated (de-convoluted) from the sequence data and the sequence targets quantified in silico after the DNA sequencing.

The advantages of the present invention include, but are not limited to quantification assay with low cost, high simplicity, high specificity, high sensitivity, high accuracy, high throughput, high scalability and high turn-over in comparison to traditional nucleic acid sequencing technologies. Another aspect of the present invention is that the methods of the present invention allow multiple samples to be pooled due to sample indexing at an initial stage of the workflow, providing improvements in assay costs and speed. Another aspect of the present invention is that the methods of the present invention allow accurate and massively parallel quantification of plurality of nucleic acid targets in multiple samples including human and animal populations, and including large volumes of unpurified sample material. As mentioned, in a preferred embodiment, the sample, such as a urine sample, is used without any prior purification or concentration of nucleic acid. In another embodiment, the sample may be pre-treated, for instance lysing cells to expose nucleic acid. One particular advantage of the invention is to enable the detection and amplification of target sequence of interest using unique probe designs, i.e., probe triplet. The probes are designed with specially situated modified nucleotides that improve annealing and binding efficiency. Improvement in binding properties leads to higher assay specificity, sensitivity and accuracy. The methods of the present invention are likewise applicable in studying genetic variants and find application in diagnosis and prognosis, including but not limited to genotype the sample(s) for one or more sequences and/or polymorphisms, such as SNPs and/or indels, cancer diagnostics or fetal chromosomal disorders from maternal blood. In a preferred embodiment, for two or more samples or for two or more locus/allele combinations, barcode sequences are used to genotype the samples for one or more sequences and/or polymorphisms, such as SNPs and/or indels.

In another aspect, the invention provides a kit of parts comprising a plurality of containers, wherein at least one container comprises one or more sets of first probe and second probe, at least one container comprises a barcode loop oligo, and at least one container comprises one or more bridge oligos or plurality of bridge oligonucleotides capable of forming a bridge oligo complex with the barcode loop oligo, wherein the first probe comprises a first bridge oligo-specific sequence at the 5' end of the first probe and a first target specific portion at the 3' end of the first probe;

wherein the second probe comprises a second target specific portion at the 5' end of the second probe and a second bridge oligo-specific sequence at the 3' end of the second probe;

wherein the barcode loop oligo comprises, starting from the 5' end of the molecule, a third bridge oligo-specific sequence, a barcoded loop sequence and a fourth bridge oligo-specific sequence, wherein the bridge oligo or plurality of bridge oligonucleotides contains sequences complementary to the first bridge oligo-specific sequence and the second bridge oligo-specific sequence in the first probe and the second probe, respectively, and sequences complementary to the third bridge oligo-specific sequence and the fourth bridge oligo-specific sequence in the barcode loop oligo;

wherein, optionally, at least one of: the first probe, the second probe, the barcode loop oligo, the bridge oligo or an oligonucleotide of the plurality of bridge oligonucleotides comprises a recognition sequence for an endonuclease;

and wherein optionally the kit of parts further comprises an oligonucleotide capable of annealing with said recognition sequence such that a recognition site for said endonuclease is obtained. Preferably, the 3' end of the first probes or the 5' end of the second probes, or both, are modified to permit chemical ligation of the first probes to the second probes.

Preferably, the bridge oligo or an oligonucleotide of the plurality of bridge oligonucleotides comprises one or more chemically modified nucleotides in the sequence complementary to a sequence of the first probe or in the sequence complementary to a sequence of the second probe, or both.

Preferably, the 3' end of the first probe or the 5' end of the second probe, or both, are modified to permit chemical ligation of the first probe to the second probe.

Preferably, the bridging portion of the first probe or the second probe, or both, or the barcode loop oligo, the bridge oligo or an oligonucleotide of the plurality of bridge oligonucleotides comprise(s) chemically modified bases to permit improved binding to the bridge oligo or bridge oligo complex.

In one particular embodiment, at least one container comprising the set of first and second probe, at least one container comprising a barcode loop oligo, and at least one container comprising the bridge oligo or a plurality of oligonucleotides capable of annealing to each other to form a bridge oligo complex, are one and the same container. In such case, the four or more probes may be pre-annealed and have formed a ligated complex.

One particular advantage of the invention is to enable the detection and amplification of target sequence of interest using unique probe designs. The probes are designed with improved binding properties lead to higher assay specificity, sensitivity and accuracy. The present invention finds application in the area of molecular biology, evolutionary biology, metagenomics, genotyping and more specifically, but not limited to cancer diagnostics or fetal chromosomal disorders, including but not limited to genotype sample(s) for one or more sequences and/or polymorphisms, such as SNPs and/or indels.

In one particular preferred embodiment, the barcode loop oligo comprises information to identify the sample and includes a unique barcode. In such case, the first and second probe is universally applicable to all samples (and only comprises information to identify the target). In one preferred embodiment, therefore, a method or a kit according to the invention is provided, wherein the barcode loop oligo comprises a barcode that comprises a unique sequence that enables enumeration of the target sequences of each sample.

EXAMPLES

Method

1. Formation of Probe Complexes

Probe complexes contain sequences required for genomic targeting, sample indexing and constructing Illumina sequencing libraries.

Four-part probe complexes are allowed to form (as illustrated in FIG. 2), comprising:
(a) a first probe having, starting from the 5' end of the molecule, a first bridge oligo-specific sequence, and a first target specific portion at the 3' end of first probe;
(b) a second probe having, starting from the 5' end of the molecule, a second target specific portion, a second sequence barcode, and a second bridge oligo-specific sequence at the 3' end of second probe;
(c) a bridge oligo having sequences complementary to the first bridge oligo-specific sequence and the second bridge oligo-specific sequence in the first probe and the second probe, respectively; and (d) a loop oligo having sequences complementary to the bridge oligo.

Probe complexes are built by combining all three parts (bridge, right arm and left arm) in equimolar amounts in annealing reaction. The reaction is carried out in a thermo cycler (Annealing program in Table 1).

TABLE 1

| Step | Temperature | Time |
|------|-------------|------|
| 1 | +95° C. | 5 min |
| 2 | +95° C. | 1 min |
|  | −4° C./cycle, go to 2 10 × |  |
| 3 | +55° C. | 10 min |
| 4 | +55° C. | 1 min |
|  | −5° C./cycle, go to 5 5 × |  |
| 5 | +4° C. | hold |

2. Target Capture

Specific genomic regions containing the mutation(s) of interest are targeted. Purified DNA (for example from tissue, plasma, urine or saliva) can be used as sample or the samples can be non-purified, but only preprocessed, for example by boiling and/or centrifugation.

The probe complexes are hybridized to target regions via base sequence complementary interactions. To initiate the target capture, reaction probes and target DNA are mixed and incubated in a thermal cycler (Target capture and GapFill program in Table 2). The pre-annealed barcode loops (with specific index sequence for each sample) are added to the targeting reaction.

TABLE 2

| Step | Temperature | Time | Process |
|------|-------------|------|---------|
| 1 | +85° C. | 4 min | denaturation |
| 2 | +75° C. | 2.5 min |  |
| 3 | +65° C. | 2.5 min |  |
| 4 | +55° C. | 120 min | target capture |
| 5 | +50° C. | 10 min | GapFill |
| 6 | +45° C. | 45 min |  |
| 7 | +4° C. | hold |  |

3. GapFill Reaction

After target capture, the probe complexes from separate targeting reactions are pooled and subsequently extended and ligated by adding a combination of Phusion DNA polymerase, nucleotides and Ampligase DNA ligase and incubating 45 minutes at +45° C.

4. Exonuclease Treatments

After GapFill linear molecules are removed by adding 1 µl of Thermolabile Exonuclease 1 (NEB, #M0568L) and 1 µl of RecJF Exonuclease (NEB, #M0264L) and incubating 30 minutes in +37° C. Exonucleases are inactivated by incubating 12 minutes in +92° C.

5. Rolling Circle Amplification

After extension and ligation, circular probe molecules are subjected to Rolling Circle Amplification (RCA). For RCA reaction target capture reaction is mixed with RCA reaction mix containing EquipPhi29 (Thermo Scientific) polymerase. Reaction is incubated at +42° C. for 30 min-2 hours. After RCA reaction the efficiency of reaction is analyzed by measuring the concentration of single stranded DNA (ssDNA) with Qubit fluorometer.

6. Enzymatic Digestion

RCA reaction produces a long concatemeric ssDNA molecule having multiple copies of target library. Each complete target library is separated by EcoRI restriction enzyme recognition sequence. This sequence permits sequence-specific cutting of the long concatemer via annealing with a specific oligonucleotide containing the EcoRI restriction enzyme recognition sequence and release of ready target libraries. RCA products are digested with EcoRI for 1 hour at +37° C.

7. Library PCR

The digested RCA products are extended into sequencing libraries in a PCR reaction where the truncated sequencing adapters present in the right probe are extended into flow-cell compatible full-length sequencing adapters.

8. Library Purification

After library PCR the library molecules are purified by extracting them from agarose gels after electrophoresis or with size selection beads (such as Macherey Nagel NucleoMag).

9. Sequencing

Purified MiSeq- or iSeq100-compatible libraries are subjected to sequence analysis using state of the art sequencing instruments. Importantly, the libraries can be converted to fit in any available sequencing platform by simple oligonucleotide modifications. Sequencing data is processed using a combination of Unix command line tools and Python and R programming languages. Briefly, the rationale for the sequence processing is to identify the probe sequences within each read, sequence the genomic area between them, and count the number of molecular barcodes associated with each genetic target.

Experiment 1

In the first experiment the probe mix was a collection of four loop-indexed probe complexes in five separate samples, where the first four samples had a single loop index and the fifth one had sampled 1-4 pooled together. They targeted four gene fusions. Target oligonucleotides had unique recognition sequences allowing identification of each target.

As a sample, three synthetic target oligonucleotides were mixed in logarithmically increasing concentrations. Target capture, extension and ligation reactions, rolling circle amplification, subsequent digestion with EcoRI and library preparation PCR were carried out as described above. An example of the resulting sequencing library is shown in FIG. 3.

Figure 4:
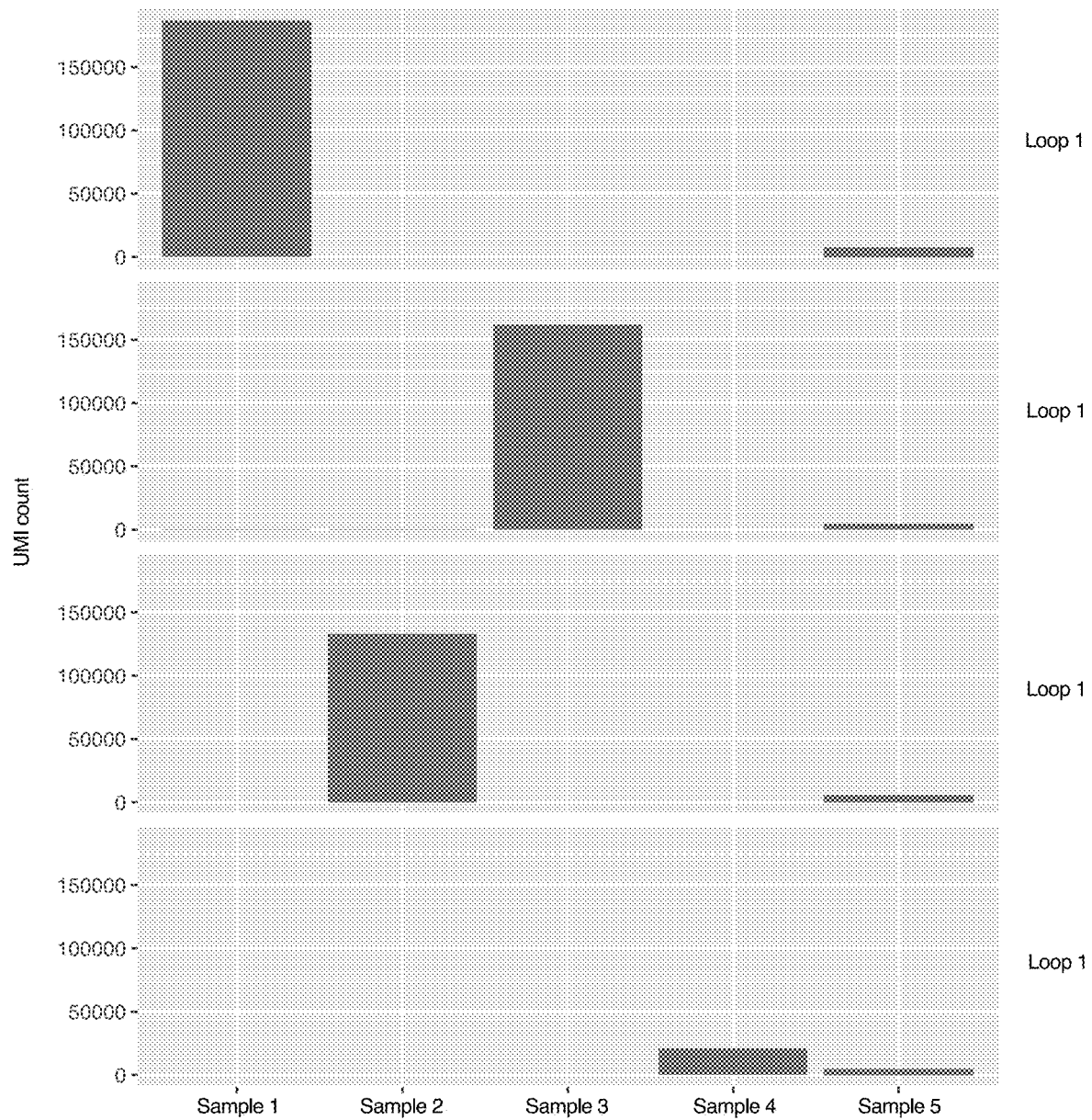
FIG. 4 illustrates the linear response of the experimental workflow to logarithmically decreasing number of genetic targets in four replicate reactions, inferred from next-generation DNA sequencing data by enumerating the molecular barcodes. Each row represents three concentrations of the target sequence. The response is linear across three orders of magnitude.

Ready libraries were sequenced with MiSeq and iSeq100 instruments and target regions were detected within the sequence data by matching the probe sequences within each read, identifying the genomic sequence area between the probe sequences and counting the molecular barcodes. The count data accurately reflected the proportions of the pooled loop oligo molecules (FIG. 4).

Detailed Description of FIGS. 1 and 2

FIG. 1 illustrates the workflow of one embodiment of the described invention. In step 1, nucleic acids (DNA or RNA) within a sample (102) are brought into contact with a set of ligation complexes (104). The ligation complexes anneal on the target nucleic acids (106). In step 2, the target-bound ligation complexes are optionally captured from the sample material, leaving behind sample impurities (103). In step 3, ligated ligation complexes from multiple samples (110) are pooled together (112). In step 4, the annealed, pooled ligation complexes are ligated, resulting in ligated ligation complexes. In step 5, the probe sequences are amplified by rolling circle amplification using phi29 polymerase or other strand displacing polymerase, resulting in long concatemeric copies of the probes (116). In step 6, the concatemeric probe copies are optionally cleaved into monomeric units using a restriction endonuclease such as EcoRI or a homing nuclease such as I-CeuI and are optionally further amplified using PCR or emulsion PCR (117). In step 7, the amplified DNA is sequenced using next-generation DNA sequencing. In step 8, the DNA sequencing results are converted into target counts using a bioinformatic pipeline.

Figure 2A:
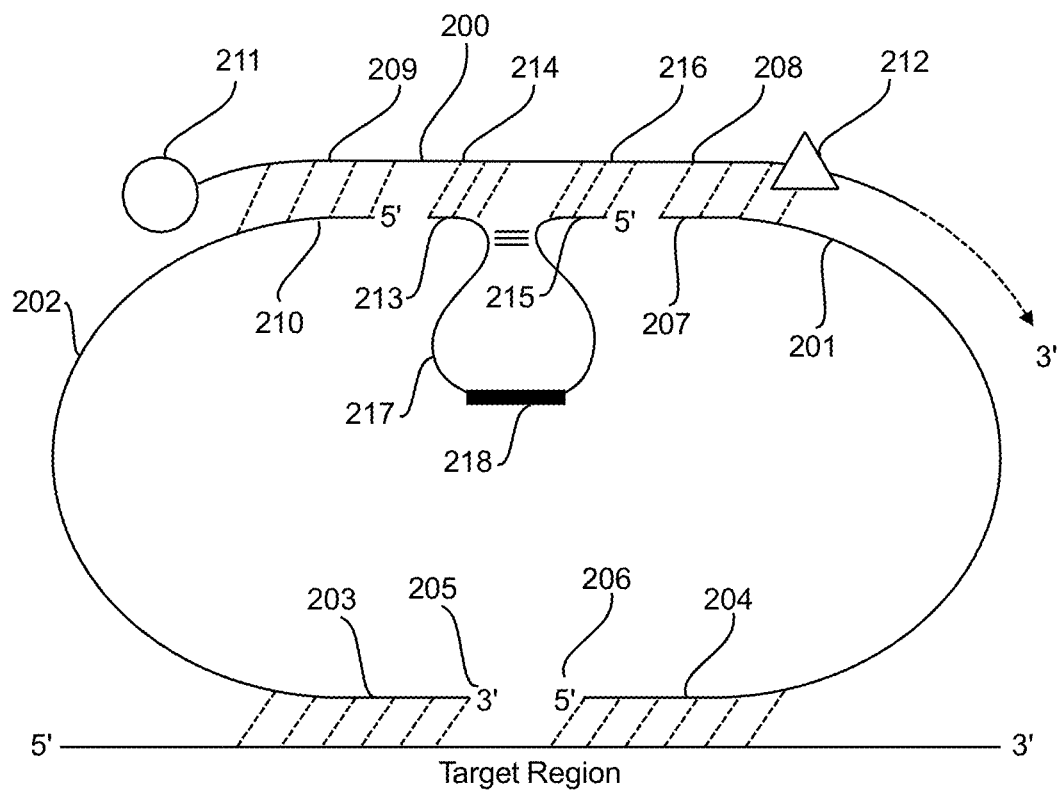
FIGS. 2A, 2B, 2C and 2D illustrate principle combinations of probes according to embodiments of the invention.

FIG. 2A illustrates a principle structure of a probe quadruplet according to an embodiment herein. The plurality of probe entities includes a first probe (202), a second probe (201), a bridge oligo (200) and a barcode loop oligo (217). Here the probe complex contains gaps or nicks between the first probe and the barcode loop oligo (210 and 213), between the second probe and the and the barcode loop oligo (207 and 215) and between the first and second probes (203 and 204). These gaps are filled by introducing a polymerase and one or more nucleotides. For this process, a mixture of Stoffel fragment, Taq polymerase or Phusion polymerase, and DNA ligase such as Ampligase can be used. The polymerase fills these gaps and the subsequent action of the DNA ligase results in ligation of the probe, bridge and barcode loop oligos into a circular complex.

15-25 bases of the first probe includes an bridge binding sequence (210), that optionally includes chemically modified bases for efficient bridge oligo binding. The first probe further includes 15-30 bases from the 5' end, binding to the genetic target (203). Some or all of the nucleotides of 210 may include chemical modifications that increase the affinity of the probes to the target or the bridge (209). The last base of the first probe optionally includes a phosphate moiety for enzymatic ligation or a modification that permits chemical ligation to the 5' end of the adjacent probe (205).

The first base of the second probe optionally includes a phosphate moiety for enzymatic ligation or a modification that permits chemical ligation to the 5' end of the adjacent probe (206). The 15-30 bases from the 5' end of the second probe include a part of the second probe that binds to the genetic target (204). The last 15-25 bases of the second probe (207), are reverse complementary to the bridge oligo (208). Some or all of the nucleotides of 203, 204, 207 or 210 may include chemical modifications that increase the affinity of the probes to the target or the bridge oligo.

The first 15-25 bases from the 5' end of the bridge oligo (209), are reverse complementary to the bridge-oligo specific sequence of the first probe (210), and optionally include chemically modified nucleotides for increased binding. The last 15-25 bases of the bridge oligo (208), are reverse complementary to the sequence of the second probe (207), and optionally include chemically modified nucleotides for increased binding. The 5' end of the bridge oligo optionally includes a capture moiety (211) used for capturing the ligation complexes. Furthermore, the bridge oligo comprises sequences 214 and 216, complementary to sequences 213 and 215 of the barcode loop oligo. The 3' end of the bridge oligo optionally includes a phosphate (or other cleavable) moiety (212) to prevent extension during gap fill.

The first 15-25 bases from the 5' end of the barcode loop oligo (215) are reverse complementary to bridge oligo sequence 216. The barcode loop oligo comprises a loop region comprising a barcode (218). The last 15-25 bases of the barcode loop oligo (213) are reverse complementary to bridge oligo sequence 214.

Figure 2B:
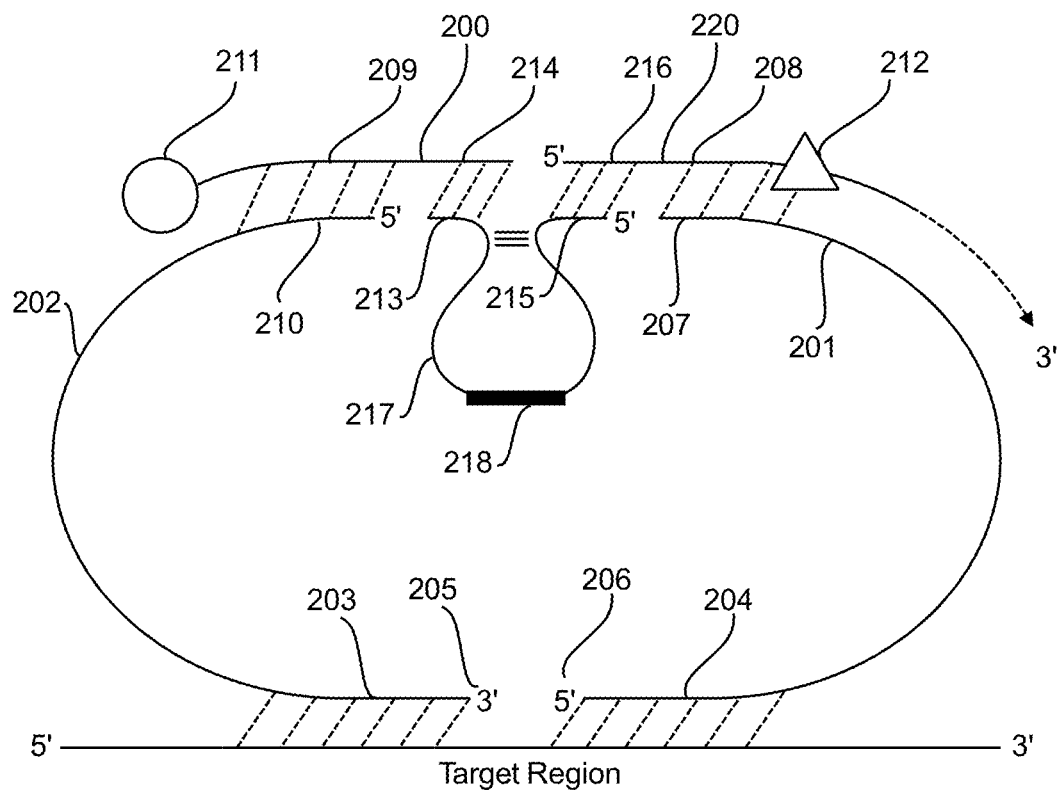

FIG. 2B illustrates a principle structure of a probe set having a plurality of probe entities according to an embodiment of the invention. The probes correspond to those of FIG. 2A, except that this embodiment comprises two bridge oligos (200 and 220), wherein bridge oligo 200 comprises 209 and 214 and bridge oligo 220 comprises 208 and 216.

Figure 2C:
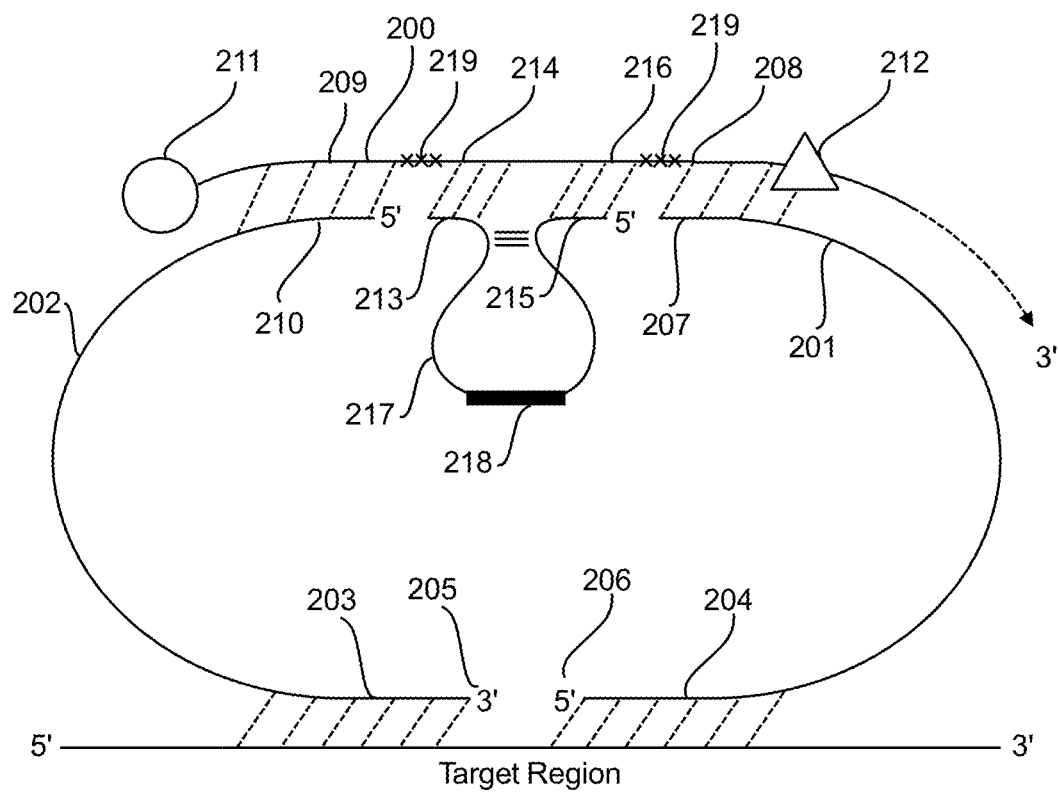

FIG. 2C illustrates a principle structure of a probe set having a plurality of probe entities according to an embodiment of the invention. The probes correspond to those of FIG. 2A, except that the bridge oligo 200 contains sequences (219) that comprise a plurality of universal base analogues to permit the incorporation of random sequences suitable for use as molecular barcode for target enumeration. One or both 219 sequences indicated may be present.

Figure 2D:
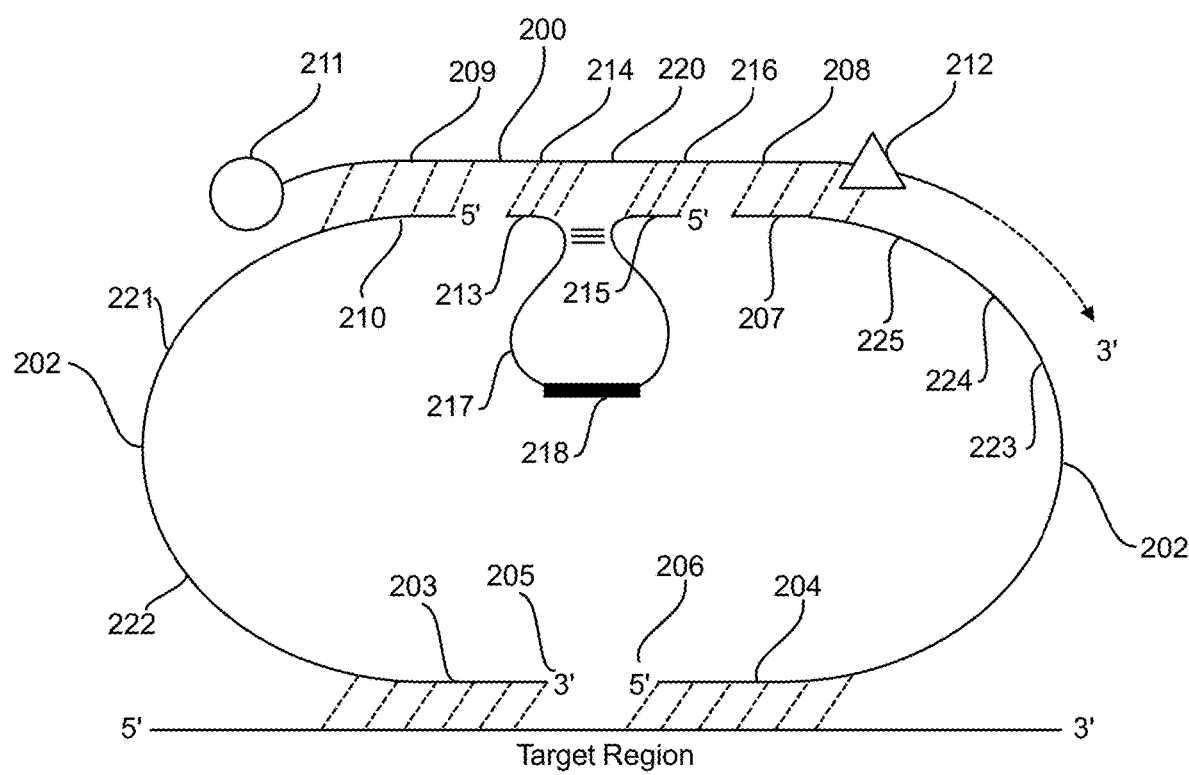

FIG. 2D illustrates a principle structure of a probe quadruplet according to an embodiment herein. The plurality of probe entities includes a first probe (202), a second probe (201), a bridge oligo (200) and a barcode loop oligo (217). Here the probe complex contains gaps between the first probe and the barcode loop oligo (210 and 213), between the second probe and the and the barcode loop oligo (207 and 215) and between the first and second probes (203 and 204). These gaps are filled by introducing a polymerase and one or more nucleotides. For this process, a mixture of Stoffel fragment, Taq polymerase or Phusion polymerase, and DNA ligase such as Ampligase can be used. The polymerase fills these gaps and the subsequent action of the DNA ligase results in ligation of the probe, bridge and barcode loop oligos into a circular complex.

15-25 bases of the first probe includes an bridge binding sequence (210), that optionally includes chemically modified bases for efficient bridge oligo binding. The first probe further includes a binding site for an amplification primer (221) and a barcode sequence (222), and 15-30 bases from the 5' end, a sequence binding to the genetic target (203). Some or all of the nucleotides of 210 may include chemical modifications that increase the affinity of the probes to the target or the bridge (209). The last base of the first probe optionally includes a phosphate moiety for enzymatic ligation or a modification that permits chemical ligation to the 5' end of the adjacent probe (205).

The first base of the second probe optionally includes a phosphate moiety for enzymatic ligation or a modification that permits chemical ligation to the 5' end of the adjacent probe (206). The 15-30 bases from the 5' end of the second probe include a part of the second probe that binds to the genetic target (204). The second probe further includes a binding site for an amplification primer (223), a sequencing adapter sequence (224), a recognition site for a restriction endonuclease such as EcoRI or a homing endonuclease (225) and another sequencing adapter sequence (207). The last 15-25 bases of the second probe (207), are reverse complementary to the bridge oligo (208). Some or all of the nucleotides of 203, 204, 207 or 210 may include chemical modifications that increase the affinity of the probes to the target or the bridge oligo.

The first 15-25 bases from the 5' end of the bridge oligo (209), are reverse complementary to the bridge-oligo specific sequence of the first probe (210), and optionally include chemically modified nucleotides for increased binding. The last 15-25 bases of the bridge oligo (208), are reverse complementary to the sequence of the second probe (207), and optionally include chemically modified nucleotides for increased binding. The part of the bridge oligo not reverse-complementary with either end of the barcode loop oligo (220) optionally contains a recognition site for a restriction endonuclease to permit enzymatic degradation of non-loop-containing structures. The 5' end of the bridge oligo optionally includes a capture moiety (211) used for capturing the ligation complexes. Furthermore, the bridge oligo comprises sequences 214 and 216, complementary to sequences 213 and 215 of the barcode loop oligo. The 3' end of the bridge oligo optionally includes a phosphate (or other cleavable) moiety (212) to prevent extension during gap fill.

The first 15-25 bases from the 5' end of the barcode loop oligo (215) are reverse complementary to bridge oligo sequence 216. The barcode loop oligo comprises a loop region comprising a barcode (218). The last 15-25 bases of the barcode loop oligo (213) are reverse complementary to bridge oligo sequence 214.

The invention claimed is:

1. A method for the high-throughput detection of one or more target nucleotide sequences in a plurality of samples, the method comprising the steps of:
   (i) providing for each target nucleotide sequence in each of the samples:
   a first probe, a second probe, a barcode loop oligo and a bridge oligo or a plurality of bridge oligonucleotides capable of annealing to the barcode loop oligo to form a bridge oligo complex,
   wherein the first probe comprises a first bridge oligo-specific sequence at the 5' end of the first probe and a first target-specific portion at the 3' end of the first probe;
   wherein the second probe comprises a second target-specific portion at the 5' end of the second probe and a second bridge oligo-specific sequence at the 3' end of the second probe;
   wherein the barcode loop oligo comprises, starting from the 5' end of the molecule, a third bridge oligo-specific sequence, a barcoded loop sequence and a fourth bridge oligo-specific sequence,
   wherein the bridge oligo or plurality of bridge oligonucleotides contains sequences complementary to the first bridge oligo-specific sequence and the second bridge oligo-specific sequence in the first probe and the second probe, respectively, and sequences complementary to the third bridge oligo-specific sequence and the fourth bridge oligo-specific sequence in the barcode loop oligo;
   and wherein, optionally, at least one of: the first probe, the second probe, the barcode loop oligo, the bridge oligo or an oligonucleotide of the plurality of bridge oligonucleotides comprises a recognition sequence for an endonuclease;
   (ii) contacting, for each of the one or more target nucleotide sequences, the first probe and the second probe with, for each of the samples in a separate tube, the barcode loop oligo and the bridge oligo or plurality of bridge oligonucleotides, and allowing self-annealing into ligation complexes, and wherein the third and fourth bridge oligo-specific sequences of the barcode loop oligo hybridize to a sequence of the bridge oligo or plurality of bridge oligonucleotides located between where the first and second bridge oligo-specific sequences of the respective first and second probes hybridize to the bridge oligo or plurality of bridge oligonucleotides;
   (iii) contacting nucleic acids present in each of the samples to be tested for the target nucleotide sequences with the ligation complexes;
   (iv) allowing the first target-specific portion and the second target-specific portion of the respective first probe and the second probe to hybridize to essentially adjacent sections on the target sequence, thereby forming hybridization complexes;
   (v) optionally pooling the hybridization complexes from the plurality of samples;
   (vi) ligating the probes in the hybridization complexes to provide ligated ligation complexes;
   (vii) amplifying nucleic acids from the one or more ligated ligation complexes using rolling circle amplification with a strand-displacing polymerase thereby obtaining single-stranded concatemeric sequences;
   (viii) optionally, provided a recognition sequence as specified in step (i) is present, performing a step to obtain nucleic acid fragments by:
      (a) cleaving the single-stranded concatemeric sequences obtained in step (vii), or
      (b) subjecting the single-stranded concatemeric sequences obtained in step (vii) to annealing with a specific oligonucleotide containing a recognition sequence for an endonuclease wherein the oligonucleotide anneals with the recognition sequence specified in step (i) such that a recognition site for the endonuclease is obtained and cleaving the annealed complexes with said endonuclease;
(ix) subjecting the concatemeric sequence obtained in step (vii) or the nucleic acid fragments obtained in step (viii) to high-throughput sequencing technology to determine the barcode sequence(s); and
(x) identifying the presence and/or number of the target nucleotide sequence in the plurality of samples by determination of at least part of the first target-specific portion and/or the second target-specific portion, and/or at least part of the barcode sequence corresponding to the barcode in the barcode loop oligo, wherein steps (v) and (vi) may be performed in any order.

2. The method according to claim 1, wherein the barcode loop oligo contains one or more recognition sequences for an endonuclease.

3. The method according to claim 2, wherein said barcode loop oligo contains two recognition sequences that are capable of annealing to each other such that a double-stranded endonuclease recognition site is obtained.

4. The method according to claim 3, wherein the method does not comprise step (viii) as specified in claim 1, but comprises, between steps (vii) and (ix), a step of allowing said two recognition sequences in the barcode loop oligo to anneal and cleaving the resulting double-stranded endonuclease recognition site with an endonuclease having specificity for said recognition site.

5. The method according to claim 1, wherein the bridge oligo, or one or more oligonucleotides of the plurality of bridge oligonucleotides, comprises, in a region not complementary to the first probe, the second probe or the barcode loop oligo, a plurality of universal base analogues to permit the incorporation of random sequences suitable for use as molecular barcode for target enumeration, and wherein, as part of step (vi), a gap filling step is performed using polymerase and nucleotides in order to generate such random sequences.

6. The method according to claim 5, wherein said plurality of universal base analogues is a plurality of 5-nitroindoles.

7. The method according to claim 1, wherein the first probe, the second probe or the bridge oligo or an oligonucleotide of the plurality of bridge oligonucleotides further comprises a sequence barcode.

8. The method according to claim 1, wherein subsequent to step (v), but prior to step (vii), a step (a) and a step (b) are performed, wherein step (a) comprises allowing the ligated ligation complexes to dissociate from the target nucleotide sequence and step (b) comprises adding a target-specific probe comprising a sequence corresponding to the target nucleotide sequence, wherein said target-specific probe is capable of annealing with the ligated ligation complexes, and allowing the target-specific probe to anneal to the ligated ligation complexes thereby forming amplification templates, and wherein, in step (vii), said amplification templates are amplified by rolling circle amplification with a strand-displacing polymerase.

9. The method according to claim 1, wherein at least one of: the first probe, the second probe, the barcode loop oligo, the bridge oligo, or an oligonucleotide of the plurality of bridge oligonucleotides, comprises a first capture moiety, and wherein between steps (iv) and (v) an intermediate step (iv)(a) is performed which comprises bringing the hybridization complexes in contact with a solid support comprising a second capture moiety, allowing the first capture moiety and the second capture moiety to interact such that the hybridization complexes become linked to the solid support and separating the solid-support-linked hybridization complexes from components of the samples that are not linked to the solid-support.

10. The method according to claim 1, wherein the plurality of samples includes a blood sample, a saliva sample, a urine sample or a feces sample.

11. The method according to claim 1, wherein the bridge oligo or an oligonucleotide of the plurality of bridge oligonucleotides comprises:
(i) one to five 3' protruding bases, and/or
(ii) 3' phosphate, and/or
(iii) one or more phosphorothioate modifications within three positions from the 3' end.

12. The method according to claim 1, wherein the 3' end of the first probe or the 5' end of the second probe, or both, are modified to permit chemical ligation of the first probe to the second probe.

13. The method according to claim 1, wherein the bridging portion of the first probe or the second probe, or both, or the barcode loop oligo, the bridge oligo or an oligonucleotide of the plurality of bridge oligonucleotides comprise(s) chemically-modified bases to permit improved binding to the bridge oligo or bridge oligo complex.

14. The method according to claim 1, wherein the first target-specific portion, the second target-specific portion, the first bridge oligo-specific sequences, and/or the second bridge oligo-specific sequences, contain independently from one another, one or more chemically-modified nucleotides.

15. The method according to claim 1, wherein the bridge oligo, or an oligonucleotide of the plurality of bridge oligonucleotides, comprises one or more chemically-modified nucleotides.

16. The method according to claim 1, wherein step (vii) is performed using a phi29 polymerase or a Bst polymerase.

17. The method according to claim 1, wherein a PCR amplification is performed immediately prior to step (ix) using primers which bind to universal parts of the first and second probes, wherein said primers optionally include adapters for subsequent sequencing in step (ix).

18. The method according to claim 1, wherein the sequencing in step (ix) is performed using nanopore sequencing, wherein optionally the concatemeric sequence obtained in step (vii) is fragmented using transposition complexes.

19. The method according to claim 1, wherein genetic target enumeration is permitted by counting the number of molecular barcodes per target and per sample.

20. The method according to claim 1, wherein for two or more samples or for two or more locus/allele combinations, barcode sequences are used to genotype the sample(s) for one or more sequences and/or polymorphisms.

* * * * *